United States Patent [19]

Ohhara et al.

[11] Patent Number: 4,996,988

[45] Date of Patent: Mar. 5, 1991

[54] METHOD OF DETERMINING BEHAVIOR OF DRUGS IN LIVING BODIES

[75] Inventors: Hiroyuki Ohhara; Akio Namimatsu; Hirohide Matsuura, all of Kato, Japan

[73] Assignee: Nippon Zoki Pharmaceutical Co., Ltd., Osaka, Japan

[21] Appl. No.: 247,280

[22] Filed: Sep. 21, 1988

[30] Foreign Application Priority Data

Sep. 22, 1987 [JP] Japan .................................. 62-238006

[51] Int. Cl.$^5$ ................................................ A61B 5/00
[52] U.S. Cl. ....................................... 128/630; 436/63
[58] Field of Search ............... 128/897, 898, 630, 632, 128/760; 424/2, 3, 9; 436/63, 174, 179, 183

[56] References Cited

U.S. PATENT DOCUMENTS

| 4,535,786 | 8/1985 | Kater | 128/630 |
| 4,537,747 | 8/1985 | Castaneda | 436/179 |
| 4,677,968 | 7/1987 | Krueger | 424/3 |

FOREIGN PATENT DOCUMENTS

| 0506395 | 6/1976 | U.S.S.R. | 128/630 |
| 0656099 | 9/1979 | U.S.S.R. | 128/630 |
| 1076810 | 2/1984 | U.S.S.R. | 128/630 |
| 1187793 | 10/1985 | U.S.S.R. | 128/630 |

Primary Examiner—C. Fred Rosenbaum
Assistant Examiner—Sharon Rose
Attorney, Agent, or Firm—Oliff & Berridge

[57] ABSTRACT

This invention provides a method of determining the behavior of drugs in living bodies, particularly those which contain a variety of active ingredients, like biological, natural drug and crude-drug preparations. It comprises administering a drug being tested to an animal, taking a blood sample from that animal, deproteinizing the plasma separated from the blood, intravenously administering the deproteinized plasma thus prepared to a different test animal, and examining the effect of drug exhibited in that test animal. The amount of active ingredients absorbed into the blood can be estimated by this indirect method even with special drugs including a variety of unknown and trace components.

4 Claims, No Drawings 4,996,988

METHOD OF DETERMINING BEHAVIOR OF DRUGS IN LIVING BODIES

BACKGROUND OF THE INVENTION

1. Field of the Invention

This invention relates to a method of determining whether or not a drug administered to an animal is absorbed into the body and distributed in the blood.

2. Description of the Prior Art

Drugs are applied orally, intravenously, intraperitoneally, rectally, intramuscularly, subcutaneously or by inhalation in the form of internal preparations, or by percutaneous absorption in the form of external preparations, and a proper method of administration is selected case by case depending on the type of drug and the kind of disease to be treated.

In any of these administration methods, it is important to make clear the actual behavior of the applied drug in living bodies, such as absorption, distribution, metabolism and excretion, in order to prove its efficacy.

Distribution of a drug absorbed in animal bodies is now measured by analysis of that drug contained int he blood or tissues through a physicochemical method, such as high-performance liquid chromatography, or by the use of drug labelled with a radioisotope.

However, some drugs containing substances extracted by a definite method from a plant or an animal treated in a specific way beforehand (like biological, natural drug and crude-drug preparations) often comprise a great variety of active components and hence exhibit the drug action as a result of synthetic effects of these components. If one tries to investigate the actual behavior of such a drug in living bodies, for example, by oral administration, by a conventional analytical method, the behavior of each of these components including unknown or trace substances must be determined. This can hardly be effected by the techniques presently available, and there has been a demand for a new method that can determine the behavior of such drugs simply and correctly.

This invention is to meet this demand.

SUMMARY OF THE INVENTION

An object of this invention is to provide a method of determining whether or not a drug, administered to an animal by a method other than intravenous injection, is absorbed through the digestive tracts, blood vessels, skin or mucous membrane and brought into the blood.

A further object of this invention is to provide a method of determining whether or not the active ingredients of a drug containing a variety of unknown or trace components (like biologicals, natural drugs and crude-drug preparations) are brought into the blood and act effectively upon the disease to be treated when it is administered by a method other than intravenous injection.

The method of this invention comprises obtaining a blood sample from an animal to which the drug to be tested has been administered, removing proteins form the plasma of said blood sample, and administering the deproteinized plasma thus obtained to a different test animal.

DETAILED DESCRIPTION OF THE INVENTION

In the method of this invention, there is no specific limitation upon the type of animal to which a drug being tested is to be administered. Any types of animals commonly employed at pharmacological experiments can be used for the purpose of this invention, including mouse, rat, guinea pig, hamster, rabbit, dog, cat, monkey, goat, sheep, pig and horse. However, use of rather small animals is advantageous in carrying out experiments as well as in terms of cost, when considering the quantity of drug to be used and the ease of animal handling. Hence, small animals, such as rats, mice, guinea pigs, hamsters, rabbits, dogs, cats and monkeys, are preferably used.

The plasma prepared from a blood sample obtained from a drug-administered animal is deproteinized by any of commonly used methods. These include treatment with a protein denaturating agent, such as organic solvents (e.g., ethanol and acetone) and acids, heating, isoelectric precipitation and salting out. The proteins separated out are then removed by filtration (through filter paper, glass filter or Celite), ultrafiltration, chromatography or centrifugation. The deproteinized plasma thus obtained may be intravenously administered to test animals without further treatment to observe the effect of the drug. Alternatively, it may be freed, prior to the intravenous administration to a test animal, from the additives such as ethanol or may be concentrated under reduced pressure to remove the solvent, followed by dilution with a suitable solvent such as distilled water to a proper concentration that allows administration to test animals.

In the method of this invention, final determination is carried out by examining the effect of the drug upon the test animal to which the deproteinized plasma has been intravenously administered. The method of this examination varies with the type of pharmacological effect of the drug being tested, and hence should be selected case by case. For example, blood pressure of test animals is measured for hypotensive agents; commonly employed analgesic tests, such as the Randall-Selitto method, are used for analgesics; and pharmacological tests to examine the conditioned-reflex suppressing effect or the like are applied in the case of drugs for mental and nervous diseases.

The following examples will further illustrate the invention but are not intended to limit its scope.

(1) Test drugs

Extract isolated form inflamed skin of rabbit inoculated with vaccinia virus [hereinafter abbreviated as "VV"; refer to Japanese Patent Publication No. 4206 (1950)], aminopyrine and diazepam were used as test drugs. Each of these was used in the form of a 0.5% CMC-Na aqueous solution for oral administration, and as a solution in physiological saline when administered intravenously.

(2) Preparation of plasma extract

A drug being tested was orally administered to a group of 60 to 120 mice, a blood sample was obtained in the presence of heparin from the abdominal aorta of each mouse under etherization after definite time intervals, and the plasma was separated from the blood. In this operation, plasma samples tinged with red (indicating hemolysis by visual observation) were not used for the experiment. Each of the plasma samples was mixed with four times its volume of ethanol, the mixture was allowed to stand for one hour, and the precipitated proteins were removed by centrifugation (4000 rpm ×

30 minutes at 4° C.). the deproteinized plasma thus obtained was freed from the solvent by treatment at 40° C. under reduced pressure, distilled water was added to prepare a plasma extract of a concentration five times as high as the original plasma, and this extract was intravenously administered to mice at the tail in an amount of 10 ml/kg to examine its pharmacological effect.

Test Example I (Analgesic Test)

Normal mice and SART (Specific Alternation of Rhythm in Temperature) stressed mice were used for this test. SART-stressed mice were prepared according to the method of Kita, et al. [Folia pharmacol. japon.; 71, 195–210 (1975)]. Mice were kept in a thermostatic box at the environmental temperature of 4° C. and 24; ° C. alternately for one hour period from 10.00 a.m. to 5.00 p.m., and at 4° C from 5.00 p.m. to 10.00 a.m. the next day. This stress loading was continued for five days prior to the test.

Pain threshold was measured for each mouse before and a definite time after administration of a test drug or plasma extract by use of the modified Randall-Selitto method (tail pressure method) as described below.

A pressure point of the Randall-Selitto apparatus was changed to a plastic plate (1.5 mm thick and 2.0 cm wide) and mechanical pressure was applied about 1.5 cm caudal from the base of the tail at a rate of 16 g/sec. The pressure intensity that caused an escape or cry reaction was defined as the pain threshold. The analgesic index was then calculated according to the equation given below, and the mice showing an analgesic index of 1.5 or higher were judged to be positive in therapeutical effect.

Analgesic Index =

$$\frac{\text{Pressure weight (g) after drug administration}}{\text{Averaged pressure weight (g) before drug administration}}$$
$(n = 2)$ The result obtained is described below.

EXPERIMENTAL RESULT (1) Time course of analgesic action

VV and aminopyrine were each administered orally or intravenously to SART stress mice, and pain threshold was measured with the passage of time. It was demonstrated that the peak of VV's action was observed 60 minutes after oral administration and 20 minutes after intravenous administration. With aminopyrine, on the other hand, the peak of action was observed 30 minutes after oral administration and 10 to 20 minutes after intravenous administration.

The analgesic action of plasma extract obtained from normal mice was then investigated upon SART stress mice.

VV (800 mg/Kg) and aminopyrine (120 mg/Kg) were each administered orally to normal mice, blood samples were obtained after 15, 30, 60, 120 and 180 minutes, and plasma extract was prepared in the same manner as described above. Each of the extract thus prepared was intravenously administered to SART stress mice, and the analgesic action was measured after 20 minutes, which is the peak action time when the drugs were directly administered intravenously. It was found that the most powerful analgesic action was observed 60 minutes after administration of VV and 30 minutes after that of aminopyrine, just as when VV or aminopyrine was directly administered orally.

(2) Analgesic action of plasma extract

Plasma extract was prepared form blood samples taken 60 minutes after oral administration of VV and 30 minutes after oral administration of aminopyrine, and each was intravenously administered to SART stress mice in an amount of 10 ml/kg. The analgesic action was measured after 20 minutes, the result of which is summarized in Table 1 below.

TABLE 1

| Plasma Extract | | Analgesic index | Effect[1] |
|---|---|---|---|
| Extract obtained from normal mice | | | |
| 0.5% CMC-Na | (20 ml/Kg) | 1.05 ± 0.06 | 0/8 |
| VV | (200 mg/Kg) | 1.43 ± 0.13* | 2/8 |
| VV | (400 mg/Kg) | 1.43 ± 0.07** | 4/8 |
| VV | (800 mg/Kg) | 1.69 ± 0.09*** | 7/8 |
| 0.5% CMC-Na | (20 ml/Kg) | 1.03 ± 0.05 | 0/8 |
| Aminopyrine | (30 mg/Kg) | 1.02 ± 0.13 | 2/8 |
| Aminopyrine | (60 mg/Kg) | 1.37 ± 0.08** | 3/8 |
| Aminopyrine | (120 mg/Kg) | 1.52 ± 0.07*** | 5/8 |
| Extract obtained from SART stress mice | | | |
| 0.5% CMC-Na | (20 ml/Kg) | 0.99 ± 0.03 | 0/8 |
| VV | (800 mg/Kg) | 1.74 ± 0.08*** | 7/8 |
| 0.5% CMC-Na | (20 ml/Kg) | 1.02 ± 0.05 | 0/8 |
| Aminopyrine | (120 mg/Kg) | 1.64 ± 0.09*** | 8/8 |

[1]Number of mice with analgesic index of 1.5 or higher/Total of mice tested
*$p < 0.05$, $p < 0.01$, *$p < 0.001$: Significantly different from respective control values; values are the mean ± S.E.

Test Example II (action to prolong the sleeping time caused by thiopental)

Test drugs and plasma extract were each administered intravenously to normal mice, thiopental (40 mg/Kg) was then intravenously administered after a definite time, the sleeping time was measured taking the loss of rightening reflex as index, and the rate of sleeping time prolongation (%) was calculated according to the equation given below, Sleep Prolongation Rate $(\%) = A/B \times 100 - 100$ wherein
A: Sleeping time for the test group
B: Sleeping time for the control group (1) Time course of the thiopental-caused sleep prolonging action VV and diazepam were each administered orally to normal mice, and the action to prolong the sleeping time caused by thiopental )40 g/Kg; intravenous administration) was examined after definite time intervals.

It was demonstrated that the peak of sleeping time prolonging action was observed 60 minutes after administration of both VV and diazepam.

Based on this fact, the dependency of sleep prolonging action upon the dose of drug was examined by intravenously administering thiopental 60 minutes after oral administration of VV and diazepam and immediately after intravenous administration of VV. The action of plasma extract obtained from normal mice to prolong the sleeping time caused by thiopental was then investigated.

VV (800 mg/Kg) and diazepam (0.8 mg/Kg) were each administered orally to normal mice, blood samples were obtained after 15, 30, 60, 120 and 180 minutes, and plasma extract was prepared in the same manner as described above. Each of the extract thus prepared was intravenously administered to normal mice to examine the sleep prolonging action.

It was found that the most powerful action was observed 30 to 60 minutes after administration of VV and 60 minutes after administration of diazepam, just as when VV or diazepam was directly administered orally.

(2) Sleep prolonging action of plasma extract

Plasma extract was prepared from blood samples obtained 60 minutes after oral administration of VV or diazepam, and each was intravenously administered to normal mice in an amount of 10 ml/Kg. The sleep prolonging action obtained is summarized in Table 2 below.

TABLE 2

| Plasma Extract | | Sleeping Time (min) | Prolonging Rate (%) |
| --- | --- | --- | --- |
| Extract obtained from normal mice | | | |
| 0.5% CMC-Na | (20 ml/Kg) | 7.4 ± 0.6 | 0 |
| VV | (200 mg/Kg) | 7.8 ± 0.5 | 5.4 |
| VV | (400 mg/Kg) | 11.5 ± 1.3* | 55.4 |
| VV | (800 mg/Kg) | 11.8 ± 0.8*** | 59.5 |
| Diazepam | (0.15 mg/Kg) | 8.4 ± 0.5 | 13.5 |
| Diazepam | (0.3 mg/Kg) | 10.2 ± 0.5** | 37.8 |
| Diazepam | (0.6 mg/Kg) | 11.3 ± 0.7*** | 52.7 |

*$P < 0.05$, $P < 0.01$, *$P < 0.001$: Significantly different from respective control values; values are the mean ± S.E.

As is apparent from the results of the analgesic and sleeping time prolonging tests described above (Test Examples I and II), it was demonstrated that, with all the drugs tested (VV, aminopyrine and diazepam), the deproteinized plasma extract obtained from an animal to which a drug has been orally administered exhibits the parmacological effect of that drug (analgesic or sleeping time prolonging action) when intravenously administered to a test animal. This clearly indicates that the orally administered drug has been absorbed through the digestive tracts and brought into the blood.

In addition, studies on the peak action time (the time after oral administration at which the plasma extract shows the most powerful action) revealed that it coincides with the peak action time when the drug is directly administered orally. This coincidence between the two peak action times also proves that the drug has been absorbed through the digestive tracts and brought into the blood, thereby exhibiting its effect.

Furthermore, the dose-dependent effect of plasma extract, as shown in the Test Examples, indicates the possibility of estimating the amount of active ingredient brought into the blood.

The fact that VV, which is a biological preparation containing a variety of active components, proved to be absorbed into the blood shows that the method of this invention is very effective in determining the absorption distribution of drugs which contain a great variety of active ingredients and hence cannot be analyzed by conventional methods such as biological, natural drug and crude-drug preparations.

What is claimed is:

1. A method of determining the behavior of drugs in living bodies which comprises administering a drug being tested to an animal by a method other than intravenous injection, deproteinizing plasma obtained from that animal, intravenously administering the deproteinized plasma thus prepared to a different test animal, and examining the effect of the drug exhibited in the test animal.

2. The method as defined in claim 1 wherein said drug is orally administered.

3. The method as defined in claim 1 wherein said drug is a biological, natural drug or crude-drug preparation.

4. The method as defined in claim 1 wherein said deproteinized plasma is diluted with distilled water to a prescribed concentration and the diluted plasma thus obtained is intravenously administered to the different test animal.

* * * * *